United States Patent [19]

Davies et al.

[11] Patent Number: 4,772,614
[45] Date of Patent: Sep. 20, 1988

[54] QUINOLONE SULPHONAMIDES USEFUL AS ANTIHYPERTENSIVE AGENTS

[75] Inventors: Roy V. Davies, Nottinghamshire; James Fraser; Kenneth J. Nichol, both of Nottingham, all of England

[73] Assignee: The Boots Company, England

[21] Appl. No.: 874,217

[22] Filed: Jun. 13, 1986

[30] Foreign Application Priority Data

Jun. 15, 1988 [GB] United Kingdom ............... 8515209

[51] Int. Cl.$^4$ .................. C07D 215/36; A61K 31/47
[52] U.S. Cl. .................................. 514/312; 546/153; 546/155; 546/156; 560/46; 548/485; 562/453; 564/86; 564/194
[58] Field of Search ................ 514/312, 314; 546/155

[56] References Cited

U.S. PATENT DOCUMENTS

| | | | |
|---|---|---|---|
| 4,302,460 | 11/1981 | Davies et al. | 546/155 |
| 4,442,109 | 4/1984 | Davies et al. | 546/153 |
| 4,447,435 | 5/1984 | Davies et al. | 546/153 |
| 4,552,884 | 11/1985 | Sim et al. | 514/312 |
| 4,659,718 | 4/1987 | Davies et al. | 546/153 |

FOREIGN PATENT DOCUMENTS

| | | |
|---|---|---|
| 0172004 | 2/1986 | European Pat. Off. . |
| 2452484 | 9/1980 | France . |
| 4913185 | 2/1974 | Japan .................. 546/155 |

OTHER PUBLICATIONS

Derwent Abstract 23901V for Japan Patent No. 49-13185 (2/5/74).
Yanagisawa et al., *Chem. Pharm. Bull.* 21(5), pp. 1080–1089 (1973).
Liebigs Annalen Der Chemie (1978) pp. 617–626.

*Primary Examiner*—Donald G. Daus
*Assistant Examiner*—E. Bernhardt
*Attorney, Agent, or Firm*—Jacobs & Jacobs

[57] ABSTRACT

Quinolones with antihypertensive activity have the general formula I,

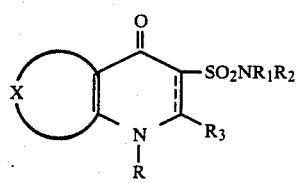

wherein X is the residue of an optionally substituted benzene ring; R is lower alkyl; $R_3$ is hydrogen or lower alkyl; $R_1$ and $R_2$, which may be the same or different, are hydrogen, lower alkyl, or, together with the nitrogen atom to which they are attached, form a 5 to 7 membered saturated heterocyclic ring optionally containing an additional hetero atom selected from nitrogen, oxygen and sulphur and optionally substituted by 1 or more lower alkyl groups; and the dotted line between positions 2 and 3 of the quinolone nucleus represents an optional bond. The compounds are useful as antihypertensive agents. They are also indicated for use in treating heart failure and ischaemic heart disease.

With the exception of the three compounds 1-methyl-4-oxo-1,4-dihydroquinoline-3-sulphonamide, 1,N-dimethyl-4-oxo-1,4-dihydroquinoline-3-sulphonamide and 6,7-dimethoxyl-methyl-4-oxo-1,4-dihydroquinoline-3-sulphonamide, the quinolones of formula I are novel.

Pharmaceutical compositions containing the compounds of formula I are described. Processes for preparing the novel quinolones are also described.

17 Claims, No Drawings

QUINOLONE SULPHONAMIDES USEFUL AS ANTIHYPERTENSIVE AGENTS

This invention relates to therapeutic compositions containing quinolones which have antihypertensive activity, to certain novel quinolones and to processes for preparing the novel quinolones.

The present invention is based on our discovery that quinolones of the general formula I,

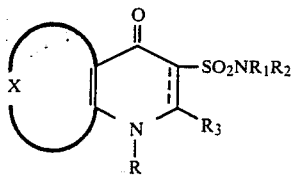

wherein X is the residue of an optionally substituted benzene ring; R is lower alkyl; $R_3$ is hydrogen or lower alkyl; $R_1$ and $R_2$, which may be the same or different, are hydrogen, lower alkyl, or, together with the nitrogen atom to which they are attached, form a 5 to 7 membered saturated heterocyclic ring optionally containing an additional hetero atom selected from nitrogen, oxygen and sulphur and optionally substituted by 1 or more lower alkyl groups; and the dotted line between positions 2 and 3 of the quinolone nucleus represents an optional bond, have antihypertensive activity. The compounds reduce blood pressure when administered to hypertensive mammals.

Three compounds within formula I have been described previously. Hiroaki Yanagisawa et al., Chem. Pharm. Bull., 21 (5), 1080–1089 (1973) describe, amongst a variety of quinoline and naphthyridine derivatives, the compounds 1-methyl-4-oxo-1,4-dihydroquinoline-3-sulphonamide, 1,N-dimethyl-4-oxo-1,4-dihydroquinoline-3-sulphonamide, 1,N-dimethyl-4-oxo-1,4-dihydroquinoline-3-sulphonamide and 6,7-dimethoxy-1-methyl-4-oxo-1,4-dihydroquinoline-3-sulphonamide. It is stated that the compounds prepared in this work were evaluated for antimicrobial activity but no significant activity was noted.

Thus novel compounds of the present invention are those of the hereinbefore defined formula I, provided that when the dotted line represents a bond, R is methyl, $R_1$ and $R_3$ are hydrogen; and (a) when $R_2$ is hydrogen, then the fused benz-ring of the 4-quinolone nucleus carries one or more substituents other than 6,7-dimethoxy; and (b) when $R_2$ is methyl, then the fused benz-ring carries at least one substituent.

More particular compounds of formula I have the formula II.

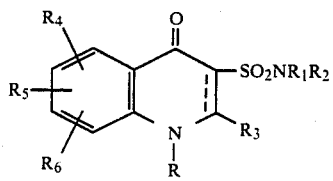

wherein R, $R_1$, $R_2$ and $R_3$ are as hereinbefore defined and $R_4$, $R_5$ and $R_6$, which may be the same or different, are hydrogen, lower alkyl, lower alkoxy, lower alkylthio, lower alkylsulphinyl, halo, fluorinated lower alkyl, fluorinated lower alkoxy, or phenyl optionally substituted by 1 to 3, especially 1 or 2, groups selected from lower alkyl, lower alkoxy, halo and trifluoromethyl.

The term "lower" signifies a group with 1 to 4 carbon atoms. The alkyl chain in the above-mentioned groups may be straight or branched and may be, for example, methyl, ethyl, n- or iso-propyl, n-, sec-, iso- or tert-butyl. The term "halo" preferably signifies fluoro, chloro or bromo. When the group —$NR_1R_2$ is a saturated heterocyclic ring it may be, for example, pyrrolidin-1-yl, piperidino, 4-methylpiperazin-1-yl, morpholino, thiomorpholino or perhydroazepin-1-yl.

In formulae I and II, preferably R is methyl or ethyl, especially methyl; $R_1$ is hydrogen or methyl and $R_2$ is methyl; and $R_3$ is hydrogen or methyl.

In formula II, $R_6$ is preferably hydrogen. Preferred values of $R_4$ and $R_5$ are hydrogen, lower alkyl, for example methyl, lower alkoxy, for example methoxy, halo, for example chloro and fluoro, and fluorinated lower alkyl, for example trifluoromethyl.

In general, the compounds of the invention in which the optional 2,3-bond is present are preferred to those in which this bond is absent. Also the compounds of the invention in which $R_3$ is hydrogen are generally preferred to those in which $R_3$ is lower alkyl.

A particularly preferred group of compounds of the present invention is that of formula IIA,

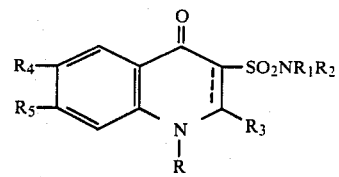

wherein the dotted line represents an optional bond; R is lower alkyl, for example methyl; $R_3$ is hydrogen or methyl; $R_1$ is hydrogen or methyl; $R_2$ is methyl; $R_4$ is hydrogen, lower alkoxy, for example methoxy, or halo, for example chloro or fluoro; and $R_5$ is hydrogen, lower alkyl, for example methyl, halo, for example chloro or fluoro, or fluorinated lower alkyl, for example trifluoromethyl.

In the compounds of formula IIA, R is preferably methyl. Especially preferred are those compounds wherein R is methyl, $R_3$ is hydrogen and the optional bond is present.

Another especially preferred group of compounds of the present invention is that of the formula IIB,

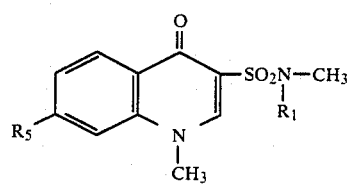

wherein $R_1$ is hydrogen or methyl and $R_5$ is hydrogen, methyl, halo or trifluoromethyl. Preferred values of halo in formula IIB are chloro and fluoro.

Particularly preferred compounds of this invention include the following novel compounds:

A: 7-chloro-1,N-dimethyl-4-oxo-1,4-dihydroquinoline-3-sulphonamide

B: 7-fluoro-1,N-dimethyl-4-oxo-1,4-dihydroquinoline-3-sulphonamide

C: 1,N-dimethyl-4-oxo-7-trifluoromethyl-1,4-dihydroquinoline-3-sulphonamide

D: 6-methoxy-1,N,N-trimethyl-4-oxo-1,4-dihydroquinoline-3-sulphonamide

E: 7-chloro-6-methoxy-1,N,N-trimethyl-4-oxo-1,4-dihydroquinoline-3-sulphonamide

Compound A is especially preferred.

It will be appreciated by those skilled in the art that, when the optional 2,3-bond is absent and $R_3$ is hydrogen, the compounds of formula I have a chiral centre and thus may exist in two enantiomeric forms. The present invention includes both enantiomers and mixtures thereof. When the optional 2,3-bond is absent and $R_3$ is methyl, the compounds of formula I have two chiral centres and thus may exist in diasterioisomeric forms. The present invention includes each of these diasterioisomeric forms and mixtures thereof.

The present invention provides pharmaceutical compositions which comprise a compound of formula I together with a pharmaceutically acceptable carrier.

In particular the compositions may comprise, as active ingredient, a novel compound of this invention.

Specific compounds which may be incorporated in the compositions of this invention are those novel compounds listed above, and in addition the following known compounds:
1-methyl-4-oxo-1,4-dihydroquinoline-3-sulphonamide
1,N-dimethyl-4-oxo-1,4-dihydroquinoline-3-sulphonamide.

As used hereinafter, the term "active compound" denotes a quinolone of general formula I. In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention suitably contain 0.1-90% by weight of active compound. The compositions of the invention are generally prepared in unit dosage form.

Compositions for oral administration are the preferred compositions of the invention and these are the known pharmaceutical forms for such administration, for example tablets, capsules, syrups and aqueous or oily suspensions. The excipients used in the preparation of these compositions are the excipients known in the pharmacist's art. Tablets may be prepared by mixing the active compound with an inert diluent such as calcium phosphate in the presence of disintegrating agents, for example maize starch, and lubricating agents, for example magnesium stearate, and tableting the mixture by known methods. Such tablets may, if desired, be provided with enteric coatings by known methods, for example by the use of cellulose acetate phthalate. Similarly capsules, for example hard or soft gelatin capsules, containing the active compound with or without added excipients, may be prepared by conventional means and, if desired, provided with enteric coatings in a known manner. Enteric coated compositions of the invention may be advantageous, depending on the nature of the active compound. The tablets and capsules may conveniently each contain 1-500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

Compositions of the invention suitable for rectal administration are the known pharmaceutical forms for such administration, for example, suppositories with cocoa butter or polyethylene glycol bases.

Compositions of the invention suitable for parenteral administration are the known pharmaceutical forms for such administration, for example, sterile suspension in aqueous and oily media or sterile solutions in a suitable solvent.

Compositions for topical administration may comprise a matrix in which the active compound is dispersed so that the compound is held in contact with the skin in order to administer the active compound transdermally. Alternatively the active compound may be dispersed in a cream or ointment base.

In some formulations it may be beneficial to use the compounds of the present invention in the form of particles of very small size, for example, as obtained by fluid energy milling.

In the compositions of the present invention the active compound may, if desired, be associated with other compatible pharmacologically active ingredients, for example a $\beta$-blocker such as propranolol, oxprenolol or timolol, or a diuretic such as bendrofluazide.

The therapeutic activity of the compounds of formula I has been demonstrated by means of tests on standard laboratory animals. Such tests include, for example, the oral administration of the compounds to a strain of spontaneously hypertensive rat and the intraduodenal administration of compounds to a strain of normotensive rat. Thus the compounds of formula I are useful for reducing blood pressure in hypertensive mammals. A suitable dose for enteral administration to mammals, including humans, is generally within the range 0.1-25 mg/kg/day, more usually 0.5-10 mg/kg/day, given in single or divided doses. For parenteral administration, a suitable dose is generally within the range 0.01-2.5 mg/kg/day, especially 0.05-1.0 mg/kg/day. Oral administration is preferred.

We have found that the compounds of formula I are vasodilators with a dilating action on both arteriolar and venous vascular beds. Accordingly the compounds are indicated for use in the treatment of ischaemic heart disease and heart failure in mammals, including humans. Suitable dosages are those given above.

The compounds of formula I in which the optional 2,3-bond is present and $R_3$ is hydrogen may be prepared by reacting a sulphonyl chloride of formula III,

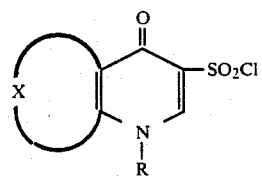

III with an amine of formula $R_1R_2NH$. The reaction may be effected using known methods used for preparing sulphonamides by reacting sulphonyl chlorides with amines.

The intermediates of formula III are novel and may be prepared by reacting a quinolone of formula IV,

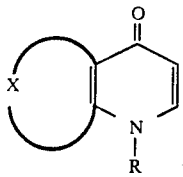

with chlorosulphonic acid. The reaction may be effected using known methods for chlorosulphonation.

The compounds of formula I in which the optional 2,3-bond is present may also be prepared by reacting a compound of formula V,

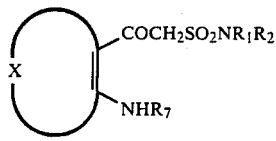

wherein $R_7$ is R, with a tri(lower alkyl) orthoalkanoate of formula $R_3C(OR_8)_3$ wherein $R_8$ is lower alkyl, preferably methyl or ethyl, for example a tri(lower alkyl) orthoformate or tri(lower alkyl) orthoacetate. The reaction may be effected by heating the reactants together in a suitable diluent, which may be a liquid inert to the conditions of the reaction or an excess of the tri(lower alkyl) orthoalkanoate. It is often advantageous for the reaction to be effected in the presence of an acid, for example, acetic acid.

The intermediates of formula V are novel, provided that, when $R_1$, $R_2$ and $R_7$ are hydrogen, X represents the residue of a benzene ring which carries at least one substituent other than lower alkyl, lower alkoxy or halo. The novel compounds of formula V may be prepared by processes analogous to those described for the known compounds of formula V by Hiroaki Yanagisawa et al., Chem. Pharm. Bull., 21 (5), 1080-1089 (1973).

The compounds of formula V wherein not more than one of $R_1$ and $R_2$ is hydrogen may be prepared by reacting a benzoic acid ester of formula VI,

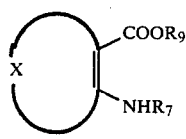

wherein $R_9$ is lower alkyl, preferably methyl or ethyl, with a lithiated methanesulphonamide of formula VII or VIII, LiCH$_2$SO$_2$NR$_1$Li      VII LiCH$_2$SO$_2$NR$_1$R$_2$      VIII In formula VII, $R_1$ is lower alkyl. In formula VIII, $R_1$ and $R_2$ are lower alkyl or, together with the nitrogen atom to which they are attached, form a heterocyclic ring as hereinbefore defined.

The compounds of formula VII and VIII are prepared by reacting the appropriate methanesulphonamide of formula IX,

CH$_3$SO$_2$NR$_1$R$_2$      IX wherein $R_1$ is lower alkyl and $R_2$ is hydrogen or lower alkyl, or $R_1$ and $R_2$, together with the nitrogen atom to which they are attached, form a heterocyclic ring as hereinbefore defined, with n-butyl lithium in a suitable liquid diluent, for example tetrahydrofuran, in an inert atmosphere and at a temperature of $-50°$ to $-80°$. To effect the subsequent reaction with the ester of formula VI, it is generally convenient to add the ester to the lithiated methanesulphonamide at $-50°$ to $-80°$ and allow the reaction mixture to gradually warm to ambient temperature.

The compounds of formula I in which the optional 2,3-bond is present and $R_3$ is hydrogen may also be prepared by alkylation of a compound of formula X.

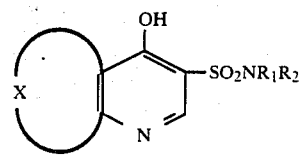

The alkylation may be effected in an appropriate manner for alkylation reactions using alkylating agents of formula R—Z wherein Z is chloro, bromo or iodo, or of formula (R)$_2$SO$_4$. When one of the groups $R_1$ or $R_2$ represents hydrogen, the conditions of alkylation should be chosen to be selective for the quinoline nitrogen atom.

The intermediates of formula X are novel, provided that, when $R_1$ and $R_2$ are hydrogen, X represents the residue of a benzene ring which carries at least one substituent other than lower alkyl, lower alkoxy or halo. The compounds of formula X may be prepared by reacting a compound of formula V wherein $R_7$ is hydrogen with a tri(lower alkyl) orthoformate, preferably trimethyl orthoformate or triethyl orthoformate.

The compounds of formula I wherein the optional bond is present, $R_1$ is hydrogen and $R_2$ is hydrogen or lower alkyl may also be prepared by debenzylation of a compound of formula XI,

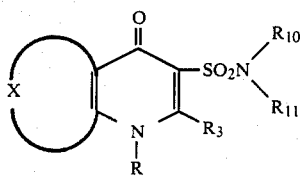

wherein $R_{10}$ is hydrogen, lower alkyl or $R_{11}$, and $R_{11}$ is benzyl or substituted benzyl capable of debenzylation, for example 4-nitrobenzyl or 4-methoxybenzyl. The debenzylation is conveniently carried out by heating the compound of formula XI with a suitable acid, for example methanesulphonic acid, trifluoroactic acid or concentrated sulphuric acid.

The intermediates of formula XI are novel and may be prepared by a reaction analogous to the hereinbefore described reaction between a compound of formula V and a tri(lower alkyl) orthoalkanoate of formula $R_3C(OR_8)_3$.

The compounds of formula XI wherein $R_3$ is hydrogen may also be prepared by reacting a compound of formula III with an amine of formula $R_{10}R_{11}NH$.

The compounds of formula I wherein $R_1$ is hydrogen or lower alkyl and $R_2$ is lower alkyl may also be prepared by alkylation of the corresponding compounds wherein $R_1$ and $R_2$ are hydrogen or $R_1$ is hydrogen and $R_2$ is lower alkyl. The alkylation may be effected by reaction with a suitable alkylating agent, for example an alkyl iodide, using reaction conditions analogous to those known in the art for the N-alkylation of sulphonamides.

The compounds of formula I wherein the optional 2,3-bond is absent may be prepared by reacting a compound of formula V wherein $R_7$ is R with an aldehyde of formula $R_3$—CHO, or a di(lower alkyl) acetal thereof. Thus, for example, reaction with formaldehyde or dimethoxymethane gives the compounds of formula I wherein the optional 2,3-bond is absent and $R_3$ is hydrogen. Paraformaldehyde may be used as a convenient source of formaldehyde.

The compounds of formula I in which the optional bond is present and which contain a 7-(lower alkoxy) or 7-(lower alkylthio) substituent may be prepared by reacting the corresponding 7-fluoro compounds with lower alkoxide ion or lower alkylthiolate ion.

The compounds of formula I in which the optional bond is present and which contain a 7-(lower alkylsulphinyl) substituent may be prepared by oxidation of the corresponding 7-(lower alkylthio) compounds using, for example, an organic percarboxylic acid as the oxidising agent.

The compounds of formula I in which the optional bond is present and which contain a 7-(fluorinated lower alkoxy) substituent may be prepared by reacting the corresponding 7-fluoro compound with hydroxide ion to give the corresponding 7-hydroxy compound, which is then reacted with the appropriate fluorinated chloroalkane, for example chlorodifluoromethane, to give the 7-(fluorinated lower alkoxy) compound, for example the 7-difluoromethoxy compound.

The compounds of formula I in which the optional bond is present and which contain a 7-fluorinated lower alkoxy group of the formula —$OCH_2R_{11}$ wherein $R_{11}$ is a fluorinated lower alkyl group, for example trifluoromethyl, may be prepared by reacting the corresponding 7-fluoro compounds with the ion $R_{11}CH_2O^-$.

The compounds of formula I in which the optional bond is present may also be prepared by oxidation of the corresponding compounds in which the 2,3-bond is absent. This oxidation may be effected in a manner similar to that known for analogous reactions. Thus the oxidation may be carried out by passing air or oxygen into a solution or suspension of the 2,3-dihydro compound in a suitable liquid, preferably in the presence of a catalyst such as palladium/carbon. Basic conditions are preferred. Thus, for example, the reaction may be carried out in aqueous sodium hydroxide with a palladium/carbon catalyst at a temperature between 20° and 80°.

As mentioned above, the therapeutic activity of the quinolones of the present invention has been demonstrated by tests which include (A) the oral administration of the compounds to a strain of spontaneously hypertensive rat and (B) the intraduodenal administration of the compounds to a strain of normotensive rat. These tests were carried out in the following way:

TEST A

Female rats, weight range 180–250 g, of the Aoki-Okamoto strain of spontaneously hypertensive rat were used. The rats in groups of four were fasted overnight before administration of the test compound. Blood pressure was determined in the following way. The rats were placed in a cabinet kept at 38° C. with their tails protruding through holes in the cabinet. After 30 minutes in the cabinet blood pressure was measured using an inflatable cuff placed round the base of the tail and arterial pulsations monitored with a pneumatic pulse transducer. A pressure, greater than the expected blood pressure, was applied to the cuff, and this pressure was slowly reduced. The pressure in the cuff at which arterial pulsations reappeared was taken as the blood pressure. The rats were removed from the cabinet and each group orally dosed with a given dose of the test compound given as a solution or suspension in 0.25% aqueous carboxymethylcellulose. In addition to the pre-dose reading, blood pressure was measured at 1.5 and 5.0 hours after dosing. A compound was designated as active if it gave a reduction of blood pressure equal to or greater than that considered to be the minimum significant reduction ($p < 0.01$) on the basis of historical control data.

TEST B

Male normotensive rats (Wistar strain) of weight range 210–240 g were used. The rats were anaesthetised and cannulae placed in a carotid artery and in the duodenum. Blood pressure was recorded electronically by means of a pressure transducer connected to the arterial cannula. The test compound was administered into the duodenum as a solution or suspension in 0.25% aqueous carboxymethylcellulose. Blood pressure was recorded before dosing and for 30 minutes afterwards. Results were obtained as the mean of determinations in three rats per dosage level. Compounds which caused an obvious drug-related fall in blood pressure of 14% or greater during the 30 minute post-dose period were designated as active.

The final products of Examples 1–21 were active in one or both of Tests A and B at a dosage of 90 mg/kg or less.

The invention is illustrated by the following non-limitative Examples, in which compositions of mixed solvents are given by volume. Novel compounds were characterised by one or more of the following spectroscopic techniques: nuclear magnetic resonance, infrared and mass spectroscopy. Temperatures are given in degrees Celsius.

EXAMPLE 1

(a) 1-Methyl-4-quinolone (2 g) was heated with chlorosulphonic acid (5 ml) at 125° for 2.5 hours. The reaction mixture was cooled to room temperature and then carefully poured onto crushed ice (300 ml). The precipitated solid was collected by filtration and then dried to give the novel compound 1-methyl-4-oxo-1,4-dihydroquinoline-3-sulphonyl chloride, m.p. 313°–315°.

(b) The above sulphonyl chloride (2 g) was added to aqueous ammonia (specific gravity 0.88; 50 ml) and stirred at room temperature for 30 minutes. The reaction mixture was extracted with dichloromethane (4×20 ml) and the extracts combined, dried over anhydrous magnesium sulphate, evaporated and the residue crystallised from methanol to give the compound 1-methyl-4-oxo-1,4-dihydroquinoline-3-sulphonamide, m.p. 230°–231°.

EXAMPLE 2

A mixture of 1-methyl-4-oxo-1,4-dihydroquinoline-3-sulphonyl chloride (2.4 g) and a solution of dimethylamine in ethanol (33% w/w; 50 ml) was stirred at room temperature for 30 minutes. The precipitated solid was filtered off and then boiled with dichloromethane (100 ml). The mixture was filtered and the filtrate evaporated to dryness to provide a white solid which was crystallised from methanol to give the novel compound 1,N,N-trimethyl-4-oxo-1,4-dihydroquinoline-3-sulphonamide, m.p. 225°–226°.

EXAMPLE 3

A mixture of 1-methyl-4-oxo-1,4-dihydroquinoline-3-sulphonyl chloride (3.56 g) and aqueous methylamine (30% w/v; 100 ml) was stirred at room temperature for 1 hour. The precipitated solid was filtered off, washed with water and crystallised from aqueous acetic acid to give the compound 1,N-dimethyl-4-oxo-1,4-dihydroquinoline-3-sulphonamide, m.p. 248°–250°.

EXAMPLE 4

(a) 7-Chloro-1-methyl-4-quinolone (6.9 g) and chlorosulphonic acid (14 ml) were stirred and heated at 140° for 2 hours. The reaction mixture was cooled to room temperature and carefully added dropwise to ice water (200 ml). The solid which formed was collected, washed with water and dried in air to give the novel compound 7-chloro-1-methyl-4-oxo-1,4-dihydroquinoline-3-sulphonyl chloride, m.p. >300°.

(b) The above sulphonyl chloride (6.5 g) and aqueous methylamine (30% w/v; 220 ml) were stirred at room temperature for 3 hours. The resulting solid was collected, washed with water and crystallised from dichloromethane/industrial methylated spirit 1:1. The product was collected and partitioned between water (200 ml) and dichloromethane (200 ml). The organic layer was separated, dried over anhydrous sodium sulphate and evaporated to dryness. The residue was crystallised from industrial methylated spirit to give the novel compound 7-chloro-1,N-dimethyl-4-oxo-1,4-dihydroquinoline-3-sulphonamide, m.p. 220°–223°.

EXAMPLE 5

(a) 1,7-Dimethyl-4-quinolone (4.31 g) was stirred with chlorosulphonic acid (11.95 ml) at 140° for 2.5 hours and then cooled to room temperature and poured carefully into ice water (1 liter). The resulting white solid was collected, washed with water and dried to give the novel compound 1,7-dimethyl-4-oxo-1,4-dihydroquinoline-3-sulphonyl chloride, m.p. >300°.

(b) The above sulphonyl chloride (3.43 g) was added to a solution of methylamine in ethanol 33% w/w; 150 ml) and stirred at room temperature for 26 hours. The mixture was partitioned between water (500 ml) and dichloromethane (500 ml). The dichloromethane layer was separated and dried over anhydrous magnesium sulphate and evaporated. The resulting solid product was crystallised from industrial methylated spirit to give the novel compound 1,7,N-trimethyl-4-oxo-1,4-dihydroquinoline-3-sulphonamide, m.p. 237°–240°.

EXAMPLE 6

(a) Iodomethane (11.6 ml) was added to a stirred suspension of 7-fluoro-4-hydroxyquinoline (25 g) and anhydrous potassium carbonate (21.7 g) in dimethylformamide (120 ml) and stirring was continued for 15 hours at room temperature. Further quantities of iodomethane (5.8 ml) and anhydrous potassium carbonate (10.85 g) were added and the mixture stirred for a further 2.5 hours at 40°. The mixture was then cooled to room temperature and poured into water (750 ml). The solid product was collected and crystallised from water to give 7-fluoro-1-methyl-4-quinolone, m.p. 146°–149°.

(b) The above quinolone (5.69 g) and chlorosulphonic acid (15.3 ml) were stirred and heated at 140° for 2 hours followed by cooling to room temperature and pouring carefully into ice water (400 ml). The resulting solid was collected by filtration, washed with water and dried to give the novel compound 7-fluoro-1-methyl-4oxo-1,4-dihydroquinoline-3-sulphonyl chloride, m.p. 194°–196°.

(c) The above sulphonyl chloride (2.51 g) was stirred with a solution of methylamine in ethanol (33% w/w; 120 ml) at room temperature for 24 hours and then added to water (300 ml) and extracted with dichloromethane (3×500 ml). The combined extracts were dried over anhydrous magnesium sulphate and evaporated to give a solid product. The solid product was then purified by high pressure liquid chromatography over silica gel and eluting with ethyl acetate. The product produced on evaporation of the ethyl acetate was crystallised from methanol to give the novel compound 7-fluoro-1,N-dimethyl-4-oxo-1,4-dihydroquinoline-3-sulphonamide, m.p. 255°–257°.

EXAMPLE 7

(a) 1-Methyl-4-oxo-7-trifluoromethyl-1,4-dihydroquinoline-3-carboxylic acid (13 g), dibutyl phthalate (125 ml) and copper powder (1.25 g) were stirred and heated at 305° for 5 minutes. The mixture was cooled to room temperature and filtered. Hydrogen chloride gas was passed into the ice cooled filtrate for 30 minutes. The resulting solid was collected and dried. The product was purified by boiling with isopropyl alcohol (100 ml), cooling the mixture to room temperature and collecting the novel compound 1-methyl-7-trifluoromethyl-4-quinolone hydrochloride, m.p. 212°–219° (dec).

(b) The above quinolone hydrochloride (11.5 g) and chlorosulphonic acid (60 ml) were stirred and heated at 120°–130° for 4 hours. The reaction mixture was then cooled to room temperature and carefully poured into ice water (400 ml). The solid product was collected, washed with water (100 ml) and dried to give the novel compound 1-methyl-4-oxo-7-trifluoromethyl-1,4-dihydroquinoline-3-sulphonyl chloride, m.p. 262°–265°.

(c) The above sulphonyl chloride (8 g) was added to a solution of methylamine in ethanol (33% w/w; 150 ml), and stirred at room temperature for 24 hours. The resulting solid was collected and stirred with water (50 ml). The product was collected and then crystallised from industrial methylated spirit with hot filtering to give the novel compound 1,N-dimethyl-4-oxo-7-trifluoromethyl-1,4-dihydroquinoline-3-sulphonamide, m.p. 218°–219°.

EXAMPLE 8

(a) Iodomethane (6.9 ml) was added to a stirred suspension of 6-fluoro-4-hydroxyquinoline (16.3 g) and anhydrous potassium carbonate (15.2 g) in dry tetrahydrofuran (100 ml) at ambient temperature and stirring was continued for 18 hours. More iodomethane (1.8 ml) and anhydrous potassium carbonate (3.8 g) were added and stirring was continued for 4 hours at ambient temperature. Concentrated aqueous ammonia (specific gravity 0.88; 100 ml) was added and the mixture was evaporated to dryness. The residue was treated with water (200 ml) and extracted with dichloromethane (2×400 ml). The extract was dried and evaporated to dryness. The residue was crystallised from ethyl acetate to give the novel compound 6-fluoro-1-methyl-4-quinolone, m.p. 88°–89°.

(b) In a similar way to that described in Example 6(b), the above quinolone was reacted with chlorosulphonic acid to give the novel compound 6-fluoro-1-methyl-4-oxo-1,4-dihydroquinoline-3-sulphonyl chloride, m.p. >300°.

(c) In a similar way to that described in Example 6(c), the above sulphonyl chloride was reacted with methylamine in ethanol. The product was isolated by partition between water and dichloromethane. There was obtained the novel compound 6-fluoro-1,N-dimethyl-4-oxo-1,4-dihydroquinoline-3-sulphonamide, m.p. 284°–285° (dec.).

EXAMPLE 9

A mixture of 7-chloro-1-methyl-4-oxo-1,4-dihydroquinoline-3-sulphonyl chloride (7.3 g) and dimethylamine (33% w/w solution in industrial methylated spirit; 150 ml) was stirred at room temperature for 72 hours. The precipitate and residue from evaporation of the filtrate were combined and crystallised from industrial methylated spirit. The product was ground under water, collected and dried to give the novel compound 7-chloro-1,N,N-trimethyl-4-oxo-1,4-dihydroquinoline-3-sulphonamide, m.p. 207°–209°.

EXAMPLE 10

1-Methyl-4-oxo-7-trifluoromethyl-1,4-dihydroquinoline-3-sulphonyl chloride (12.4 g) was added to a stirred solution of dimethylamine in industrial methylated spirit (33% w/w; 230 ml) and the mixture was kept at ambient temperature for 27 hours. The mixture was evaporated to dryness and the residue was recrystallised from industrial methylated spirit using charcoal to give the novel compound 1,N,N-trimethyl-4-oxo-7-trifluoromethyl-1,4-dihydroquinoline-3-sulphonamide, m.p. 221°–223°.

EXAMPLE 11

(a) 7-Chloro-1-methyl-4-oxo-1,4-dihydroquinoline-3-sulphonyl chloride (9.2 g) was added portionwise to a stirred solution of benzylamine (10.5 ml) in absolute alcohol (300 ml). The mixture was stirred at ambient temperature for 24 hours, then evaporated to dryness. The residue was crystallised from industrial methylated spirit to give the novel compound N-benzyl-7-chloro-1-methyl-4-oxo-1,4-dihydroquinoline-3-sulphonamide, m.p. 208°–210°.

(b) The above N-benzylsulphonamide (2.4 g) was added to methanesulphonic acid (25 ml) heated on a steam bath. The mixture was stirred and heated for 10 minutes, poured on to ice (150 g), and neutralised with saturated aqueous sodium bicarbonate. The resulting solid product was collected, dried and crystallised from industrial methylated spirit to give the novel compound 7-chloro-1-methyl-4-oxo-1,4-dihydroquinoline-3-sulphonamide, m.p. 235°–237°.

EXAMPLE 12

(a) To a stirred solution of N-methylmethanesulphonamide (13.6 g) in dry tetrahydrofuran (160 ml) at −70° to −60° was added a solution of n-butyl lithium in hexane (2.5M; 100 ml) under argon. The mixture was stirred at −78° for 1 hour and a solution of methyl 2-amino-3,4,5-trimethoxybenzoate (10 g) in dry tetrahydrofuran (50 ml) was added at −70° to −60°. The mixture was stirred for 2 hours, during which time the temperature rose to 10°. The mixture was poured on to ice (500 g), acidified to pH 1 with 5N HCl, and then neutralised to pH 7 with saturated aqueous sodium bicarbonate. The solid product was extracted into dichloromethane (3×500 ml). The extract was dried and evaporated to give a residue. This residue was triturated with ether to give a solid which was collected, dried and crystallised from ethyl acetate to give the novel compound 1-(2-amino-3,4,5-trimethoxyphenyl)-2-(N-methylsulphamoyl)ethanone, m.p. 125°–127°.

(b) A mixture of the above ethanone (7.41 g) and triethyl orthoformate (150 ml) was stirred and heated to boiling. Glacial acetic acid (1 ml) was added and the stirred mixture was boiled under reflux for 50 minutes. The mixture was cooled to ambient temperature. The solid product was collected by filtration, washed with diethyl ether and dried to give the novel compound 4-hydroxy-6,7,8-trimethoxy-N-methylquinoline-3-sulphonamide, m.p. 254°–255°.

(c) A mixture of the above sulphonamide (6.1 g), anhydrous potassium carbonate (1.28 g), dry dimethylformamide (100 ml), and iodomethane (1.16 ml) was stirred and heated at 40° for 18 hours, left at ambient temperature for 72 hours, and heated at 40° for 6 hours. More iodomethane (01.58 ml) and potassium carbonate (0.64 g) were added and the mixture stirred at 40° for 48 hours. The mixture was filtered and the filtrate evaporated to dryness to give a residue which was extracted with boiling industrial methylated spirit (250 ml). The extract was cooled to give a precipitate which was recrystallised from industrial methylated spirit to give the novel compound 6,7,8-trimethoxy-1,N-dimethyl-4-oxo-1,4-dihydroquinoline-3-sulphonamide, m.p. 184°–186°.

EXAMPLE 13

(a) In a similar manner to that described in Example 12(a), N-methylmethanesulphonamide was reacted with n-butyl lithium and the product was reacted with ethyl 2-amino-5-methoxybenzoate to give the novel compound 1-(2-amino-5-methoxyphenyl)-2-(N-methylsulphamoyl)ethanone, m.p. 117°–118°.

(b) In a similar manner to that described in Example 12(b), the above ethanone was reacted with triethyl orthoformate to give the novel compound 4-hydroxy-6-methoxy-N-methylquinoline-3-sulphonamide, m.p. 293°–294°.

(c) A mixture of the above sulphonamide (1.96 g), anhydrous potassium carbonate (0.68 g) and dry dimethylformamide (50 ml) was stirred at ambient temperature for 1 hour. Iodomethane (0.6 ml) was added and the mixture stirred at 40° for 4.5 hours. After cooling to ambient temperature, concentrated aqueous ammonia (specific gravity 0.88; 2 ml) was added and stirring continued for 30 minutes. The mixture was evaporated to dryness. The residue was boiled with industrial methylated spirit (50 ml) for 30 minutes. The insoluble material was collected, washed with water and industrial methylated spirit and dried to give the novel compound 6-methoxy-1,N-dimethyl-4-oxo-1,4-dihydroquinoline-3-sulphonamide, m.p. 262°–264°.

EXAMPLE 14

(a) In a similar manner to that described in Example 12(a), N,N-dimethylmethanesulphonamide was reacted with n-butyl lithium and the product was reacted with ethyl 2-amino-5-methoxybenzoate to give the novel compound 1-(2-amino-5-methoxyphenyl)-2-(N,N-dimethylsulphamoyl)ethanone, m.p. 198°–200°.

(b) In a similar manner to that described in Example 12(b), the above ethanone was reacted with triethyl orthoformate to give the novel compound 4-hydroxy-6-methoxy-N,N-dimethylquinoline-3-sulphonamide, m.p. >300°.

(c) In a similar manner to that described in Example 13(c), the above sulphonamide was methylated with iodomethane for 15.5 hours at ambient temperature to give the novel compound 6-methoxy-1,N,N-trimethyl-4-oxo-1,4-dihydroquinoline-3-sulphonamide, m.p. 199°–201° (from industrial methylated spirit).

EXAMPLE 15

(a) To a stirred solution of chloral hydrate (123.5 g) in water (1650 ml) was added a solution of anhydrous sodium sulphate (500 g) in water (640 ml) followed by sodium sulphate decahydrate (644 g). A solution of 4-methoxy-3-methylaniline (94 g) in a mixture of concentrated hydrochloric acid (59 ml) and water (400 ml) was then added, followed by a solution of hydroxylamine hydrochloride (151 g) in water (690 ml). The mixture was boiled for 5 minutes and then left at room temperatue overnight. The solid product was collected, washed with water and dried to give the novel compound, N-(4-methoxy-3-methylphenyl)-2-hydroxyiminoacetamide, m.p. 163°–165°.

(b) The above acetamide (50 g) was added portionwise during 45 minutes to concentrated sulphuric acid (130 ml), keeping the temperature at 65°–70°. The mixture was stirred for a further 10 minutes and poured on to ice (1 kg). The solid product was collected, washed with water and dried to give the novel compound 5-methoxy-6-methyl-1-H-indol-2,3-dione, mixed with some 5-methoxy-4-methyl-1-H-indol-2,3-dione, m.p. of mixture 182°–184°.

(c) Hydrogen peroxide (100 volume, 80 ml) in water (600 ml) was added dropwise during 1.5 hours to a stirred solution of the above indol-2,3-diones (56 g) and sodium hydroxide (100 g) in water (1800 ml), keeping the temperature below 35°. The solution was acidified to pH 4 with dilute sulphuric acid (2.5M). The resulting solid was collected, washed with water and dried to give the novel compound 2-amino-5-methoxy-4-methylbenzoic acid, m.p. 193°–196°.

(d) A mixture of the above benzoic acid (31.8 g), dry ethanol (500 ml) and concentrated sulphuric acid (10 ml) was boiled under reflux for 60 hours. Most of the solvent was removed by evaporation and the residue was poured into excess saturated aqueous sodium bicarbonate. The mixture was extracted with dichloromethane (3×300 ml). The extract was dried and evaporated to give an oil which solidified on standing to give the novel compound ethyl 2-amino-5-methoxy-4-methylbenzoate. The remaining aqueous reaction liquors were acidified to pH 2 with concentrated hydrochloric acid, evaporated to dryness and the solid residue extracted with boiling dry ethanol (2×500 ml). Concentrated sulphuric acid (20 ml) was added to the extract and the mixture boiled under reflux for 60 hours. The mixture was worked up in a similar manner to that described above to give a further quantity of ethyl 2-amino-5-methoxy-4-methylbenzoate, m.p. 60°–62°.

(e) In a similar manner to that described in Example 12(a), N,N-dimethylmethanesulphonamide was reacted with n-butyl lithium and the product reacted with the above benzoate ester to give the novel compound (1-(2-amino-5-methoxy-4-methylphenyl)-2-(N,N-dimethylsulphamoyl)ethanone, m.p. 228°–230° (dec.) (from industrial methylated spirit/ethyl acetate/dichloromethane 1:1:1).

(f) In a similar manner to that described in Example 12(b), the above ethanone was reacted with triethyl orthoformate to give the novel compound 4-hydroxy-6-methoxy-7,N,N-trimethylquinoline-3-sulphonamide, m.p. 295°–297°.

(g) In a similar manner to that described in Example 13(c), the above sulphonamide was methylated with iodomethane at ambient temperature to give the novel compound 6-methoxy-1,7,N,N-tetramethyl-4-oxo-1,4-dihydroquinoline-3-sulphonamide, m.p. 232°–233° (from industrial methylated spirit).

EXAMPLE 16

(a) A mixture of ethyl 7-chloro-6-fluoro-4-hydroxyquinoline-3-carboxylate (67 g), sodium hydroxide (12 g), water (350 ml) and industrial methylated spirit (175 ml) was boiled under reflux for 65 hours. The mixture was cooled to ambient temperature and acidified to pH 1 with concentrated hydrochloric acid. The resulting precipitate was collected, washed with water and dried to give the novel compound 7-chloro-6-fluoro-4-hydroxyquinoline-3-carboxylic acid, m.p. 263°–265° (dec).

(b) The above carboxylic acid (10.0 g) was heated to fusion under argon with stirring until evolution of carbon dioxide had ceased (10 minutes). The mixture was cooled to room temperature. The solid product was washed with ethyl acetate and dried to give the novel compound 7-chloro-6-fluoro-4-hydroxyquinoline, m.p. >300°.

(c) A mixture of the above 4-hydroxyquinoline (38.5 g), potassium hydroxide (31 g) and water (500 ml) was stirred at room temperature and dimethyl sulphate (36 ml) was added dropwise during 10 minutes. After stirring for 4 hours, more dimethyl sulphate (10 ml) was added dropwise and stirring was continued for another 15 hours. Concentrated aqueous ammonia (specific gravity 0.88; 100 ml) was added and stirring continued for 1 hour. The solid product was collected, washed with water, dried and crystallised from ethyl acetate containing a trace of industrial methylated spirit to give the novel compound 7-chloro-6-fluoro-1-methyl-4-quinoline, m.p. 227°–228° (dec).

(d) In a similar manner to that described in Example 4(a), the above quinolone (10.0 g) was reacted with chlorosulphonic acid (25 ml) at 140° for 1 hour to give the novel compound 7-chloro-6-fluoro-1-methyl-4-oxo-1,4-dihydroquinoline-3-sulphonyl chloride, m.p. >300°

(e) The above sulphonyl chloride (8.65 g) was added portionwise during 15 minutes to a stirred solution of methylamine in ethanol (33%; 200 ml) at 0°–5°. The mixture was stirred for 3 hours, then evaporated to dryness. The residue was stirred with water, filtered, washed with more water, dried, crystallised from industrial methylated spirit/ethyl acetate 1:1 and recrystallised from industrial methylated spirit/water 9:1 to give the novel compound 7-chloro-6-fluoro-1,N-dimethyl-4-oxo-1,4-dihydroquinoline-3-sulphonamide, m.p. 235°–236°.

EXAMPLE 17

(a) In a similar manner to tht described in Example 12(a), N,N-dimethylmethanesulphonamide was reacted with n-butyl lithium and the product reacted with ethyl 2-amino-4-chloro-5-methoxybenzoate to give the novel compound 1-(2-amino-4-chloro-5-methoxyphenyl)-2-(N,N-dimethylsulphamoyl)ethanone, m.p. 59°–62°.

(b) In a similar manner to that described in Example 12(b), the above ethanone was reacted with thiethyl orthoformate to give the novel compound 7-chloro-4-hydroxy-6-methoxy-N,N-dimethylquinoline-3-sulphonamide, m.p. 316°–318°.

(c) In a similar manner to that described in Example 13(c), the above 4-hydroxyquinoline was methylated with iodomethane at ambient temperature to give the novel compound 7-chloro-6-methoxy-1,N,N-trimethyl-4-oxo-1,4-dihydroquinoline-3-sulphonamide, m.p. 133°–135° (dec) (from methanol).

EXAMPLE 18

7-Chloro-6-fluoro-1-methyl-4-oxo-1,4-dihydroquinoline-3-sulphonyl chloride (8.73 g) was added to a stirred solution of dimethylamine in ethanol (33%; 170 ml) at ambient temperature. The mixture was stirred for 70 hours and then evaporated to dryness. The residue was stirred with water (50 ml) for 30 minutes. The solid product was collected, dried and crystallised from industrial methylated spirit to give the novel compound 7-chloro-6-fluoro-1,N,N-trimethyl-4-oxo-1,4-dihydroquinoline-3-sulphonamide, m.p. 219°–221° (dec).

EXAMPLE 19

(a) In a similar manner to that described in Example 12(a), N-methylmethanesulphonamide was reacted with n-butyl lithium and the product reacted with methyl 4-fluoro-2-methylaminobenzoate to give the novel compound 1-(4-fluoro-2-methylaminophenyl)-2-(N-methylsulphamoyl)ethanone, m.p. 140°–142°.

(b) A mixture of the above ethanone (5.0 g), paraformaldehyde (0.58 g) and glacial acetic acid (100 ml) was boiled under reflux for 4 hours. The solution was evaporated to dryness and saturated aqueous sodium bicarbonate (30 ml) was added. The mixture was extracted with ethyl acetate (3×50 ml). The combined extracts were dried and evaporated to give a solid residue which was triturated with diethyl ether (50 ml). The product was collected and dried to give the novel compound 7-fluoro-1,N-dimethyl-4-oxo-1,2,3,4-tetrahydroquinoline-3-sulphonamide, m.p. 134°–136°.

EXAMPLE 20

A mixture of 1-(4-fluoro-2-methylaminophenyl)-2-(N-methylsulphamoyl)ethanone (6.0 g) and triethyl orthoacetate (50 ml) was stirred and heated at 120° for 20 hours, then boiled under reflux for 16 hours. The mixture was filtered and the filtrate was evaporated to dryness. The residue was extracted with dichloromethane/methanol 4:1 (30 ml), leaving a residue of product (crop 1). More product (crop 2) was obtained from the extract by flash chromatography [described in J. Org. Chem. 43, 2923–5 (1978)] over a silica gel sold under the trade name Kieselgel 60 (particle size 0.040–0.063 mm) by E. Merck of Darmstadt, W. Germany using dichloromethane/methanol 4:1 as the eluent. The two crops of product were combined and crystallised from methanol/diethyl ether 1:3 to give the novel compound 7-fluoro-1,2,N-trimethyl-4-oxo-1,4-dihydroquinoline-3-sulphonamide, m.p. 184°.

EXAMPLE 21

(a) In a similar manner to that described in Example 12(a), N,N-dimethylmethanesulphonamide was reacted with n-butyl lithium and the product reacted with methyl 4-fluoro-2-methylaminobenzoate to give the novel compound 1-(4-fluoro-2-methylaminophenyl)-2-(N,N-dimethylsulphamoyl)ethanone, m.p. 120°–124°.

(b) A mixture of the above ethanone (3 g) and triethyl orthoacetate (27 ml) was boiled under reflux for 48 hours, then cooled to ambient temperature. The solid product was collected and recrystallised from industrial methylated spirit to give the novel compound 7-fluoro-1,2,N,N-tetramethyl-4-oxo-1,4-dihydroquinoline-3-sulphonamide, m.p. 244°–247.5°.

EXAMPLE 22

In the preparation of capsules, 100 parts by weight of active compound and 250 parts by weight of lactose are de-aggregated and blended. The mixture is filled into hard gelatin capsules, each capsule containing 100 mg of active compound.

EXAMPLE 23

Tablets are prepared from the following ingredients.

|                      | parts by weight |
|----------------------|-----------------|
| Active compound      | 100             |
| Lactose              | 100             |
| Maize starch         | 22              |
| Polyvinylpyrrolidone | 10              |
| Magnesium stearate   | 3               |

The active compound, the lactose and some of the starch are de-aggregated, blended and the resulting mixture is granulated with a solution of the polyvinylpyrrolidone in ethanol. The dry granulate is blended with the magnesium stearate and the rest of the starch. The mixture is then compressed in a tableting machine to give tablets containing 100 mg active compound.

EXAMPLE 24

Tablets are prepared by the method of Example 23. The tablets are enteric coated in a conventional manner using a solution of 20% cellulose acetate phthalate and 3% diethyl phthalate in ethanol/dichloromethane 1:1.

EXAMPLE 25

In the preparation of suppositories, 100 parts by weight of active compound is incorporated in 1300 parts by weight of tri-glyceride suppository base and the mixture formed into suppositories each containing 100 mg of active compound.

What is claimed is:

1. A quinolone of the formula IIA

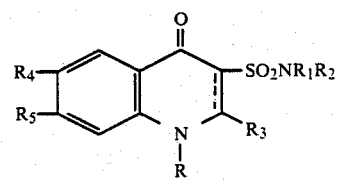

wherein the dotted line represents an optional bond; R is alkyl of 1 to 4 carbon atoms; $R_3$ is hydrogen or methyl; $R_1$ is hydrogen or methyl; $R_2$ is methyl; $R_4$ is hydrogen, alkoxy of 1 to 4 carbon atoms or halo; and $R_5$ is hydrogen, alkyl of 1 to 4 carbon atoms, halo or fluoro alkyl of 1 to 4 carbon atoms; provided that when the dotted line represents a bond, R is methyl and $R_1$ and $R_3$ are hydrogen, and the fused benzene ring carries at least one substituent.

2. A quinolone according to claim 1 wherein the optional bond is present, R is methyl and $R_3$ is hydrogen.

3. A quinolone according to claim 2 wherein $R_4$ is hydrogen, methoxy, chloro or fluoro, and $R_5$ is hydrogen, methyl, chloro, fluoro or trifluoromethyl.

4. A quinolone according to claim 3 wherein $R_4$ is hydrogen.

5. The quinolone according to claim 1 which is 7-Chloro-1,N-dimethyl-4-oxo-1,4-dihydroquinoline-3-sulphonamide.

6. A pharmaceutical composition in unit dosage form useful for treating hypertension in humans which comprises an antihypertensively effective amount of a quinolone of the formula IIA

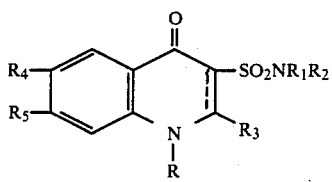

wherein the dotted line represents an optional bond; R is alkyl of 1 to 4 carbon atoms; $R_3$ is hydrogen or methyl; $R_1$ is hydrogen or methyl; $R_2$ is methyl; $R_4$ is hydrogen, alkoxy of 1 to 4 carbon atoms or halo; and $R_5$ is hydrogen, alkyl of 1 to 4 carbon atoms, halo or fluoro alkyl of 1 to 4 carbon atoms, in combination with a pharmaceutically acceptable carrier.

7. A pharmaceutical composition according to claim 6 wherein the optional bond is present, R is methyl and $R_3$ is hydrogen.

8. A pharmaceutical composition according to claim 7 wherein $R_4$ is hydrogen, methoxy, chloro or fluoro and $R_5$ is hydrogen, methyl, chloro, fluoro or trifluoromethyl.

9. A pharmaceutical composition according to claim 8 wherein $R_4$ is hydrogen.

10. A pharmaceutical composition according to claim 6 wherein the quinolone is 7-chloro-1,N-dimethyl-4-oxo-1,4-dihydroquinoline-3-sulphonamide.

11. A method of treating hypertension in humans which comprises administering to a human in need thereof an antihypertensively effective amount of a quinolone of the formula IIA

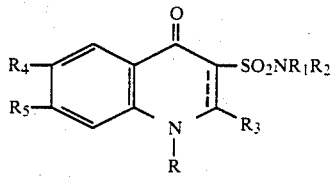

wherein the dotted line represents an optional bond; R is alkyl of 1 to 4 carbon atoms; $R_3$ is hydrogen or methyl; $R_1$ is hydrogen or methyl; $R_2$ is methyl; $R_4$; is hydrogen, alkoxy of 1 to 4 carbon atoms or halo; and $R_5$ is hydrogen, alkyl of 1 to 4 carbon atoms, halo or fluoro alkyl of 1 to 4 carbon atoms, in combination with a pharmaceutically acceptable carrier.

12. A method according to claim 11 wherein the quinolone is 7-chloro-1,N-dimethyl-4-oxo-1,4-dihydroquinoline-3-sulphonamide.

13. A method according to claim 11 wherein the optional bond is present, R is methyl and $R_3$ is hydrogen.

14. A method according to claim 13 wherein $R_4$ is hydrogen, methoxy, chloro or fluoro and $R_5$ is hydrogen, methyl, chloro, fluoro or trifluoromethyl.

15. A method according to claim 14 wherein $R_4$ is hydrogen.

16. A compound of the formula XII

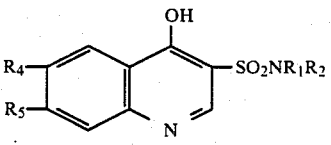

wherein $R_1$ is hydrogen or methyl; $R_2$ is methyl; $R_4$ is hydrogen, alkoxy of 1 to 4 carbon atoms or halo and $R_5$ is hydrogen, alkyl of 1 to 4 carbon atoms, halo or fluoro alkyl of 1 to 4 carbon atoms.

17. A compound of the formula XIII

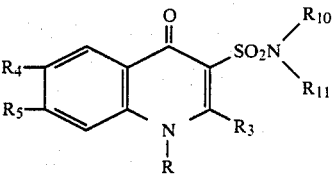

wherein R is alkyl of 1 to 4 carbon atoms; $R_3$ is hydrogen or methyl; $R_4$ is hydrogen, alkoxy of 1 to 4 carbon atoms or halo; $R_5$ is hydrogen, alkyl of 1 to 4 carbon atoms, halo or fluoro alkyl of 1 to 4 carbon atoms; $R_{10}$ is hydrogen, alkyl of 1 to 4 carbon atoms or $R_{11}$, and $R_{11}$ is benzyl, 4-nitrobenzyl or 4-methoxybenzyl.

* * * * *